United States Patent [19]

van Andel

[11] Plant 5,133

[45] Nov. 8, 1983

[54] ALSTROEMERIA NAMED STAKAROS

[75] Inventor: Jacob van Andel, Aalsmeer, Netherlands

[73] Assignee: B. V. Handelskwekerij/M. C. van Staaveren, Aalsmeer, Netherlands

[21] Appl. No.: 331,149

[22] Filed: Dec. 16, 1981

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Chas. W. Rummler

[57] ABSTRACT

A new alstroemeria cultivar similar in most respects to King Cardinal (U.S. Plant Pat. No. 4,634) and distinguished by having pink and yellow flower petals, the outer row of petals each having a pink body overcast with a more-or-less central blotch of dark pink which occasionally extends to the petal tip and the petals of the inner row being of a yellowish hue overcast by short, longitudinally-extending pencil stripes of a brown color and having a dark pink coloration at the flower throat.

1 Drawing Figure

BACKGROUND OF THE NEW PLANT

This new variety of alstroemeria originated as a sport of King Cardinal (U.S. Plant Pat. No. 4,634) and is generally similar in its physical aspects and growth habit. This plant was discovered by me at Aalsmeer, The Netherlands, in 1979 and because of its very notable differences from its parent, it was asexually propagated under my direction for test and observation. Successive generations of the plant, propagated by division of root stock, have demonstrated that it has retained the physical characteristics of the discovery plant and its parent, with the exception of its novel flower color, and that this novelty holds true from generation to generation and appears to be firmly fixed.

DESCRIPTION OF THE DRAWING

My new alstroemeria cultivar is illustrated by the accompanying photographic drawing, which shows the distinguishing color characteristics of the plant and the flower form, the color rendition being hand painted and as nearly true as it is reasonably possible to obtain by conventional professional procedures.

DESCRIPTION OF THE NEW PLANT

The following is a detailed description of my new alstroemeria cultivar with color designations according to the R.H.S. Colour Chart of The Royal Horticultural Society of London, England.

THE PLANT

Origin: Sport.

Parentage: King Cardinal (U.S. Plant Pat. No. 4,634).

Classification:

*Botanic.*—Alstroemeria L.

*Commercial.*—Alstroemeria.

Form:

*Herb.*—A tall, slender flowering stalk with flower bearing branches in simple umbel form at its top.

Height: About 1.50 m.

Growth: Vigorous, strong and upright.

Root stock:

*Tuberous.*—The tubers bear many buds from which the flower stalks grow in various stages of development during the year.

Branching: Each flower stalk branches at the top to form an umbel of flower bearing stems.

Foliage: Abundant, with 20 to 30 leaves per stem.

*Leaf size.*—Various, depending on season.

*Shape.*—Long elliptic with rounded apex.

*Texture.*—Soft, leathery.

*Color.*—Upper side — Middle Green.

Rhizomes: Number and size varying with the season.

*Color.*—White.

THE BUD

Form: Pear-shaped and of medium size.

*Diameter.*—About 1 cm.

*Length.*—About 2 cm.

Opening: Slowly.

Calyx: This bud has no calyx and the six petals of the flower are a perianth.

Peduncle:

*Length.*—About 10 cm.

*Character.*—The peduncle is sturdy and extends at an angle of about 60° relative to the main stem.

THE FLOWER

Blooming habit: Continuous and profuse during early Spring and Fall blooming seasons.

Flower size: Large.

*Diameter.*—About 5.50 to 6.00 cm.

*Depth.*—About 4 cm.

Shape: Generally funnel-like.

Borne: Singly on a long peduncle from a long and sturdy stem.

Petalage:

*Number of petals.*—Six.

*Arrangement.*—Two concentric circles of three petals each.

*Form.*—Wide elliptic with slight serration at outer end.

*Texture.*—Soft appearance; shiny.

*Color.*—Outer petal: Upper side — RHS 48C with medial blotch of 48A. Outer side — RHS 48C with 48A. Inside petal: RHS 48C with about inner two-thirds RHS 14B and with 48A at the throat, substantially the entire petal being marked with short longitudinal stripes of RHS 166A.

*Peduncle.*—Long, strong and upright, length depending upon growing season.

Persistence: The flowers hang on and dry.

Lasting quality:

*On plant.*—About 14 days.

*As cut flower.*—About 7 days.

REPRODUCTIVE ORGANS

Stamens:

*Number.*—Six, there being one opposite each petal.

*Anthers.*—Length — About 7 mm. Color: Yellow-Green.

*Filaments.*—Length — About 4 cm. Color: Red with white base.

*Pollen.*—Color — Yellow.

Pistils:

*Number.*—One.

*Style.*—Length — About 6 mm.

*Stigma.*—Color — Red.

This alstroemeria variant of King Cardinal is most nearly like its parent in substantially all respects except for the exceptional color variation in its flowers. The difference is outstanding and the plant is an attractive addition to the alstroemeria market.

I claim:

1. A new and distinctive alstroemeria plant, substantially as herein shown and described, characterized by the pink and yellow coloration of its large and profusely blooming flowers borne on strong, upstanding stems.

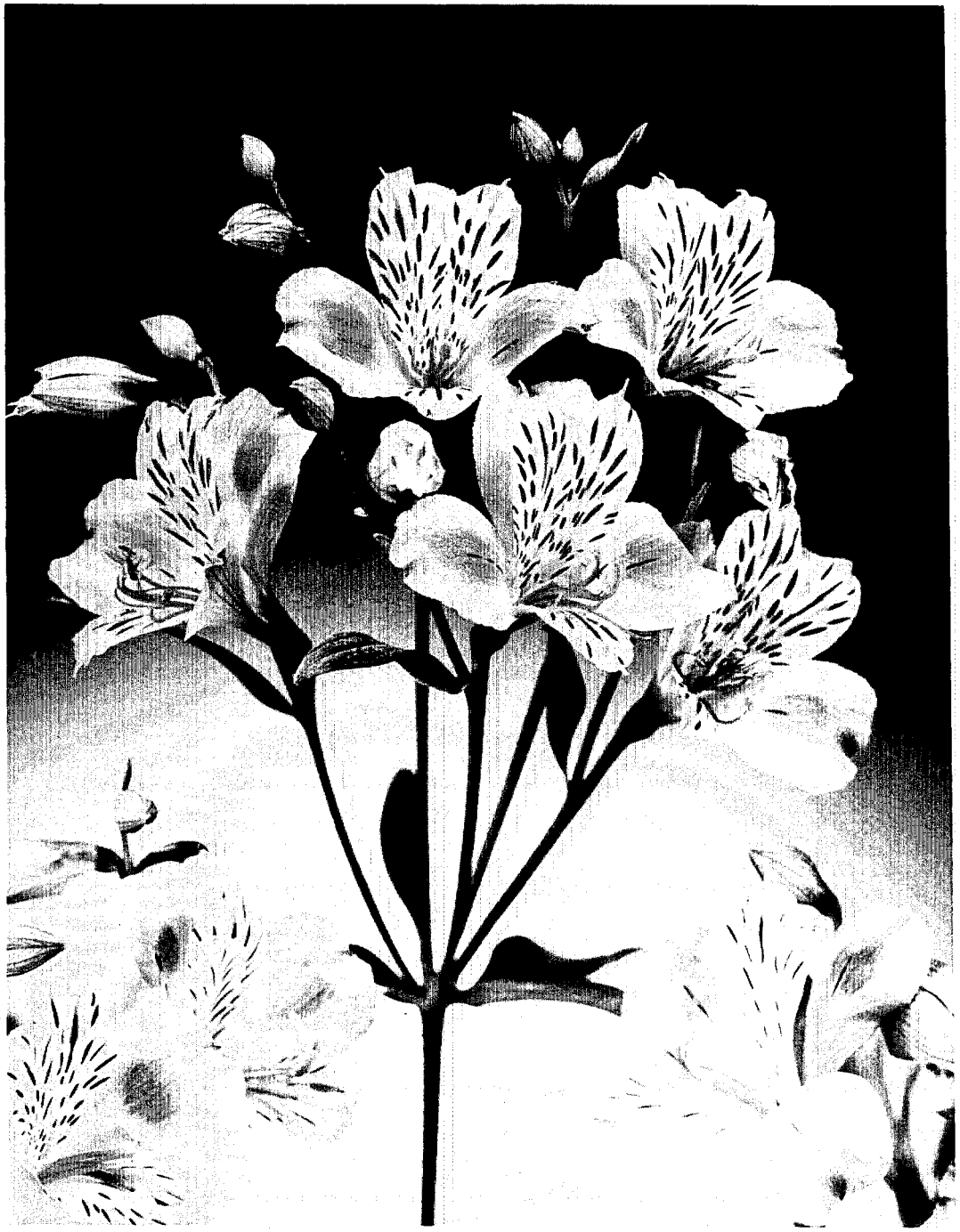

* * * * *